(12) United States Patent
Dudee (10) Patent No.: US 11,980,571 B2
(45) Date of Patent: May 14, 2024

(54) DEVICE INSERTION TOOL

(71) Applicant: Jitander Dudee, Lexington, KY (US)

(72) Inventor: Jitander Dudee, Lexington, KY (US)

( * ) Notice: Subject to any disclaimer, the term of this patent is extended or adjusted under 35 U.S.C. 154(b) by 967 days.

(21) Appl. No.: 16/934,053

(22) Filed: Jul. 21, 2020

(65) Prior Publication Data

US 2021/0022916 A1 Jan. 28, 2021

Related U.S. Application Data

(60) Provisional application No. 62/876,895, filed on Jul. 22, 2019.

(51) Int. Cl.
*A61F 9/00* (2006.01)
*A61F 9/008* (2006.01)

(52) U.S. Cl.
CPC ............ *A61F 9/0008* (2013.01); *A61F 9/008* (2013.01); *A61F 2009/00887* (2013.01)

(58) Field of Classification Search
CPC .................... A61F 9/0008; A61F 9/008; A61F 2009/00887
See application file for complete search history.

(56) References Cited

U.S. PATENT DOCUMENTS

| | | | |
|---|---|---|---|
| 5,309,187 A | 5/1994 | Crossman et al. | |
| 2005/0288745 A1 | 12/2005 | Andersen et al. | |
| 2010/0134759 A1 | 6/2010 | Silvestrini et al. | |
| 2014/0354951 A1* | 12/2014 | Izatt ...................... | A61B 3/117 351/206 |
| 2015/0313465 A1 | 11/2015 | Graham et al. | |

* cited by examiner

*Primary Examiner* — Phong Son H Dang
(74) *Attorney, Agent, or Firm* — Black McCuskey (57) ABSTRACT

A device insertion tool can include a body and a light redirecting structure. The body can extend along a central longitudinal axis between forward and aft ends. The body can include a device mount portion at the forward end to hold an optic and a handle portion at the aft end configured to be held. The body can be inserted into an anterior chamber of the eye with the optic mounted on the device mount portion at the forward end. The light redirecting structure can be engaged with the body between the forward and aft ends. The light redirecting structure can be one of at least one mirror and at least one prism. The light redirecting structure can be directed at the forward end and can be configured to redirect light traveling from the forward end toward the aft end transverse to the central longitudinal axis.

20 Claims, 8 Drawing Sheets

DEVICE INSERTION TOOL

CROSS-REFERENCE TO RELATED APPLICATIONS

This application claims the benefit of U.S. Provisional Patent Application Ser. No. 62/876,895, filed on Jul. 22, 2019, which is hereby incorporated by reference in its entirety.

BACKGROUND

1. Field

The present disclosure relates to a tool for inserting structures such as a device, an implant, a stent, or an instrument, that is to be applied in the anterior chamber of an eye, in a location that is not normally visible without a goniolens.

2. Description of Related Prior Art

U.S. Pub. No. 2015/0313465 discloses an UNREVERSED PRISM GONIOSCOPY LENS ASSEMBLY. A double-reflecting contact lens assembly for viewing the anterior chamber of an eye is provided. The lens assembly includes: (a) a lens body having a contact end defining at least a portion of first surface and a viewing end defining at least a portion of a second surface, wherein the lens body is a prism having an optical axis and magnification in the range of greater than 1× to about 2×; (b) a first reflecting surface disposed adjacent the lens body; and (c) a second reflecting surface disposed adjacent the lens body opposing the first reflecting surface. Other embodiments of the present disclosure include methods of making the lens assembly, methods of use, and a lens and handle assembly.

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

SUMMARY

A device insertion tool can include a body and a light redirecting structure. The body can extend along a central longitudinal axis between a forward end and an aft end. The body can include a device mount portion at the forward end configured to hold an optic during insertion of the optic in an eye. The body can also include a handle portion at the aft end configured to be held by a healthcare provider during insertion of the optic in the eye. The body can be configured to be inserted into an anterior chamber of the eye, through an incision in a cornea of the eye, with the optic mounted on the device mount portion at the forward end during positioning of the optic in the eye. The light redirecting structure can be engaged with the body between the forward end and the aft end. The light redirecting structure can be one of at least one mirror and at least one prism. The light redirecting structure can be directed at the forward end and can be configured to redirect light traveling from the forward end toward the aft end transverse to the central longitudinal axis.

BRIEF DESCRIPTION OF THE DRAWINGS

The detailed description set forth below references the following drawings.

DETAILED DESCRIPTION

The present disclosure, as demonstrated by the exemplary embodiment described below, provides a tool that can be utilized to place any device, implant, or instrument in the anterior chamber of the eye in a location that is not normally visible without a goniolens. A device, as that term is used herein, can be something that alters the structure of the trabecular meshwork or angle such as an implantable stent, a cutting instrument, a cautery, a laser tip, a depot of drug or other medication, or a lens haptic/stanchion. The tool can include a mirror, an array of mirrors, a prism, or an array of prisms that can be utilized by the physician to see the placement of the device during the insertion process. As a result, placement of the device can be improved.

A plurality of different embodiments of the present disclosure is shown in the Figures of the application. Similar features are shown in the various embodiments of the present disclosure. Similar features across different embodiments have been numbered with a common reference numeral and have been differentiated by an alphabetic suffix. Similar features in a particular embodiment have been numbered with a common two-digit, base reference numeral and have been differentiated by a different leading numeral. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

Figure 1:
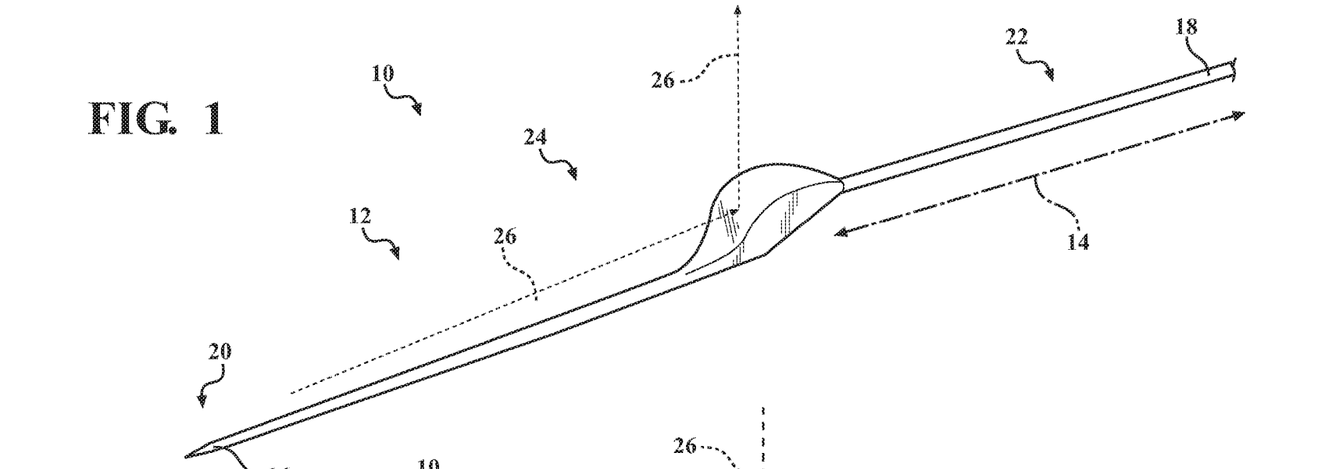
FIG. 1 is a perspective view of a device insertion tool according to a first exemplary embodiment of the present disclosure.
Figure 2:
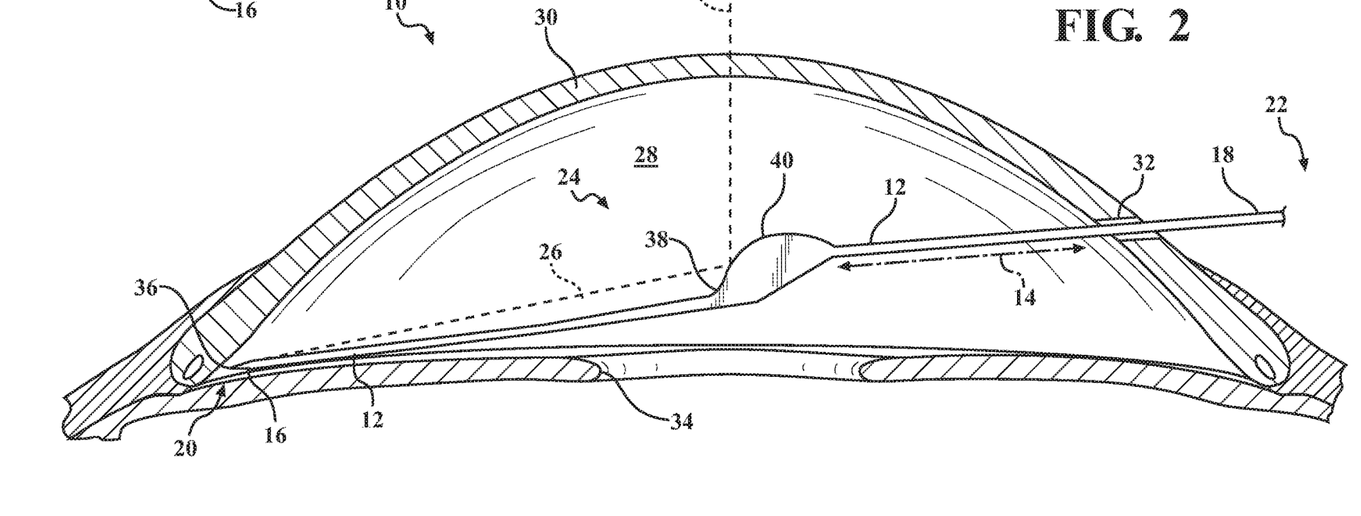
FIG. 2 is a side view of the first exemplary embodiment of the present disclosure positioned within the anterior chamber of an eye.
Figure 3:
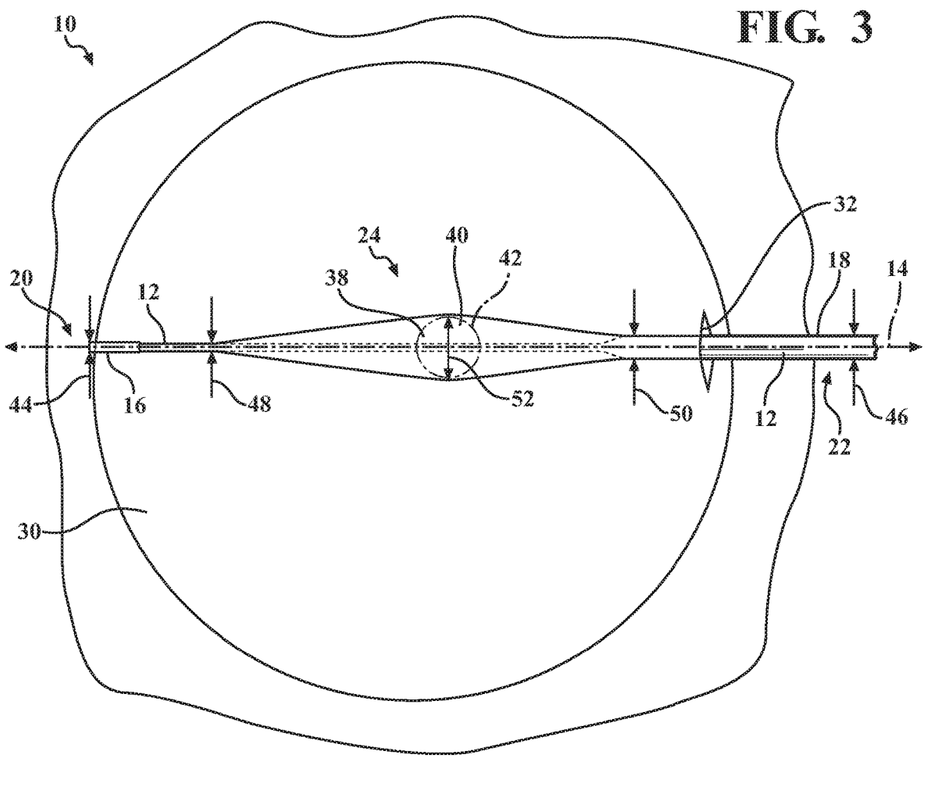
FIG. 3 is a top view of the first exemplary embodiment of the present disclosure positioned within the anterior chamber of an eye.
Figure 4:
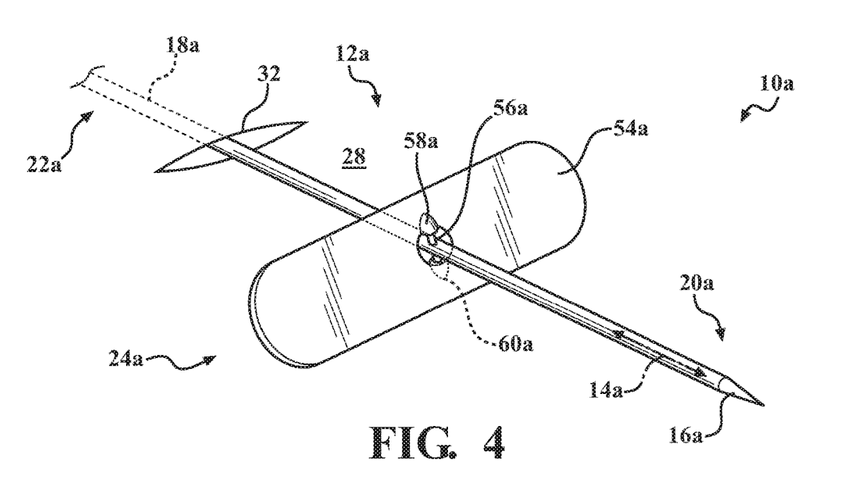
FIG. 4 is a perspective view of a device insertion tool according to a second exemplary embodiment of the present disclosure positioned within the anterior chamber of an eye.

In a first embodiment of the present disclosure, shown in FIGS. 1-3, a device insertion tool 10 includes a body 12. The exemplary body 12 extends along a central longitudinal axis 14 between a forward end 16 and an aft end 18. The exemplary body 12 terminates at the forward end 16. The exemplary body 12 includes a device mount portion 20 at the forward end 16. The exemplary device mount portion 20 is configured to hold a device during insertion of the device in an eye. One exemplary device that can be inserted in an eye with the device insertion tool 10 is a stent, such as the iStent® product which is manufactured by the Glaukos Corporation, 229 Avenida Fabricante San Clemente CALIFORNIA 92672. The exemplary device mount portion 20 can shaped to include a piercing tip to form an opening for the device in the tissue of the eye and also a tubular portion to hold the device prior to insertion and guide movement of the eye during insertion. U.S. Pat. Nos. 7,879,079, 9,301,875, 9,554,940, and 9,597,230 disclose various device mount portions and are hereby incorporated by reference for such disclosures. It is noted that the device mount portion is schematically shown as a pointed tip in the Figures.

It is noted that, in other embodiments of the present disclosure, other structures can be applied to mount a device. For example, structures that can grasp a device, such as articulating fingers, can be utilized in one or more other embodiments of the present disclosure. Further, approaches other than mechanical grasping/guiding can be applied. For example, in one or more other embodiments of the present disclosure, a device can be mounted to a device mount portion using magnetism.

The exemplary body 12 also includes a handle portion 22 at the aft end 18. The exemplary handle portion 22 is configured to be held by a healthcare provider during insertion of the device in the eye. A healthcare provider can be an ophthalmologist and/or an eye surgeon. The exemplary body 12 is configured to be inserted into an anterior chamber of the eye, through an incision in a cornea of the eye, with the device mounted on the device mount portion 20 at the forward end 16. In FIG. 2, the anterior chamber is referenced at 28, the cornea is referenced at 30, the incision at 32, the pupil is referenced at 34, and the trabecular meshwork is referenced at 36. A device such as an stent can be inserted into the trabecular meshwork 36 using the device insertion tool 10.

The device insertion tool 10 also includes a light redirecting structure 24 engaged with the exemplary body 12 between the forward end 16 and the aft end 18. Engagement between the light redirecting structure 24 and the exemplary body 12 can be defined by the two elements being integrally formed. "Integrally-formed" refers to the components that are formed together rather than being formed separately and then subsequently joined. The term defines a structural feature since structures that are integrally-formed are structurally different than structures that are comprised of subcomponents formed separately and then subsequently joined. "Integral" means consisting or composed of parts that together constitute a whole and thus encompasses structures of more than one part wherein the parts are either integrally-formed or formed separately and then subsequently joined. Engagement between the light redirecting structure 24 and the exemplary body 12 can also be defined by the light redirecting structure 24 mounted on the exemplary body 12.

The exemplary light redirecting structure 24 is also configured to be inserted into the anterior chamber 28 of the eye, through the incision 32 in the cornea 30 of the eye during positioning of the device in the eye. The light redirecting structure 24 can be at least one mirror or at least one prism. The light redirecting structure 24 can be directed at the forward end 16 and can be configured to redirect light traveling from the forward end 16 toward the aft end 18 transverse to the central longitudinal axis 14. The light traveling from the forward end 16 is light that is reflected off structures in the anterior chamber angle of the eye. The redirected light can be seen by the healthcare provider and thus allows the healthcare provider to see the location of insertion of the device in the eye without the need for an external goniolens to overcome Total Internal Reflection within the eye. In FIG. 2, the arrows referenced at 26 represents the movement of light from the forward end 16, which is also the location of insertion of the device in the eye, and redirection of the light transverse to the central longitudinal axis 14 for viewing by the healthcare provider.

The device insertion tool 10 can be sized to be able to fit within a typical anterior chamber dimensions: volume—170 μL, central depth—3 mm, and diameter—12.5 mm. Further, the device insertion tool 10 can be sized to be able to fit within a typical corneal incision. A preferred incision for most surgery of the anterior segment of the eye (surgery on the lens, internal cornea or iris) is a self-sealing arcuate incision in the corneal periphery with a chord length of 3 mm or less. For the incision to remain stable and not require corneal sutures for closure, it must remain undistorted during surgery so that the normal fluid pressure within the eye keeps it sealed. Embodiments of the present disclosure incorporate the light redirecting structure 24 in a shape that does not distort or traumatize the corneal incision 32 by virtue of having a smooth external surface, flat or minimally curved profile and a width small enough to pass through the corneal incision 32 without distortion of the corneal incision 32.

The exemplary body 12 and the exemplary light redirecting structure 24 are integrally formed and unitary. As best shown in FIG. 2, the exemplary light redirecting structure 24 includes a first surface portion 38 that faces and is concave toward the forward end 16. The exemplary light redirecting structure 24 also includes a second surface portion 40 that faces and is convex toward the forward end 16. The exemplary first surface portion 38 and the exemplary second surface portion 40 adjacent to one another and blend together. The exemplary first surface portion 38 and the exemplary second surface portion 40 are polished surfaces and cooperatively define a mirror. Light reflected off of the location of insertion of a device within the eye is redirected off of the at least one of the first surface portion 38 and the second surface portion 40.

There are no hard edges defined between the exemplary first surface portion 38 and the exemplary second surface portion 40. This arrangement allows the healthcare provider to adjust the anterior-posterior position as well as the roll, pitch and yaw of the exemplary body 12 to locate an optimum orientation of the exemplary body 12, the orientation that yields the best view of the point of insertion of the device. The circle in dash line, referenced at 42, defines a reflection zone including infinite points of reflection for the healthcare provider to utilize. A concave reflecting element can allow magnification of the object of view at specific points relative to the device insertion tool 10 to further allow precise and accurate placement of the forward end 16 and any attached device. A convex reflecting element can allow a wider field of view to allow easier orientation of the forward end 16 relative to anatomical landmarks within the eye. The minification caused by the convex mirror can be compensated for by increasing magnification of a surgical microscope used in conjunction with the device insertion tool 10. An aspheric reflecting element can minimize optical aberrations. Embodiments of the present disclosure can be practiced with various combinations of concave, convex, spherocylindrical, plane and aspheric surfaces.

Widths of various portions of the device insertion tool 10 are defined long an axis perpendicular to the central longitudinal axis 14. The widths of the forward end 16 and the aft end 18 are referenced at 44 and 46, respectively, in FIG. 3. A width of the exemplary light redirecting structure 24 varies along the central longitudinal axis 14. The width of the exemplary light redirecting structure 24 at a forward-most portion of the exemplary light redirecting structure 24 (closest to the forward end 16) is referenced at 48 and has a first value. The width of the exemplary light redirecting structure 24 at an aft-most portion of the exemplary light redirecting structure 24 (closest to the aft end 18) is referenced at 50 and has a second value. The width of the exemplary light redirecting structure 24 at a position between the first position and the second position along the central longitudinal axis 14 is referenced at 52 and has a third value. The third value greater than the first value and greater than the second value. The exemplary body 12 and the exemplary light redirecting structure 24 have substantially the same width at the first portion and the second portion. A maximum width of the exemplary light redirecting structure 24 (width referenced at 52) is greater than a maximum width of the forward end 16 (width referenced at 44). The varying width of the light redirecting structure 24 enhances insertion of the light redirecting structure 24 through the incision 32 by elimination the likelihood that the light redirecting structure 24 might snag on the incision 32. The exemplary device insertion tool 10 can be introduced and withdrawn with minimal distortion of and trauma to the corneal incision 32.

In a second embodiment of the present disclosure, shown in FIGS. 4-7, a device insertion tool 10a includes a body 12a. The exemplary body 12a extends along a central longitudinal axis 14a between a forward end 16a and an aft end 18a. The exemplary body 12a terminates at the forward end 16a. The exemplary body 12a includes a device mount portion 20a at the forward end 16a. The exemplary device mount portion 20a is configured to hold a device during insertion of the device in an eye.

The exemplary body 12a also includes a handle portion 22a at the aft end 18a. The exemplary handle portion 22a is configured to be held by a healthcare provider during insertion of the device in the eye. A healthcare provider can be an ophthalmologist and/or an eye surgeon. The exemplary body 12a is configured to be inserted into an anterior chamber of the eye, through an incision in a cornea of the eye, with the device mounted on the device mount portion 20a at the forward end 16a. In FIGS. 4-7, the anterior chamber is referenced at 28, the cornea is referenced at 30, the incision at 32, the pupil is referenced at 34, and the trabecular meshwork is referenced at 36. A device such as an stent can be inserted into the trabecular meshwork 36 using the device insertion tool 10a.

Figure 5:
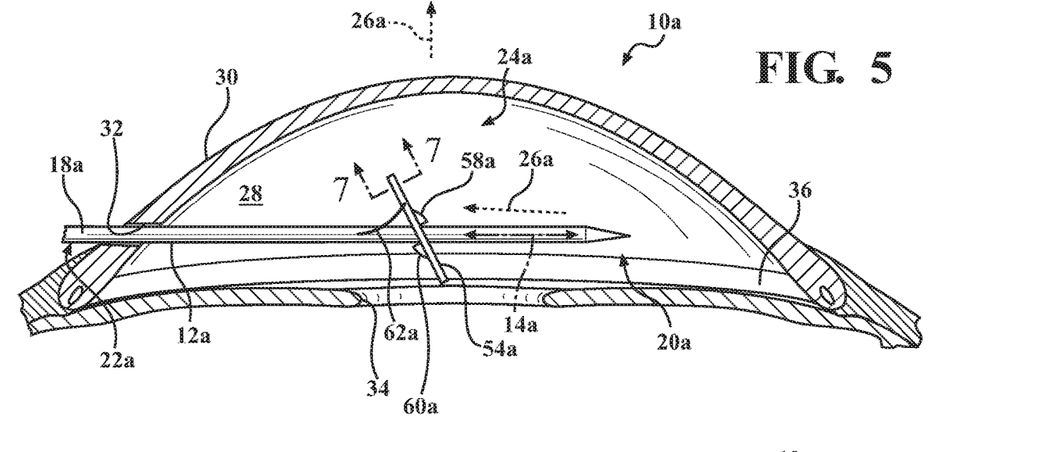
FIG. 5 is a side view of the second exemplary embodiment of the present disclosure positioned within the anterior chamber of an eye.

The device insertion tool 10a also includes a light redirecting structure 24a engaged with the exemplary body 12a between the forward end 16a and the aft end 18a. Engagement between the light redirecting structure 24a and the exemplary body 12a can be defined by the light redirecting structure 24a mounted on the exemplary body 12a. The exemplary light redirecting structure 24a is also configured to be inserted into the anterior chamber 28 of the eye, through the incision 32 in the cornea 30 of the eye during positioning of the device in the eye. The light redirecting structure 24a can be at least one mirror or at least one prism. The light redirecting structure 24a can be directed at the forward end 16a and can be configured to redirect light traveling from the forward end 16a toward the aft end 18a transverse to the central longitudinal axis 14a. The light traveling from the forward end 16 is light that is reflected off of the structures of the eye. The redirected light can be seen by the healthcare provider and thus allows the healthcare provider to see the location of insertion of the device in the eye. In FIG. 5, the arrows referenced at 26a represents the movement of light from the forward end 16a, which is also the location of insertion of the device in the eye, and redirection of the light approximately transverse to the central longitudinal axis 14a for viewing by the healthcare provider.

Figure 6A:
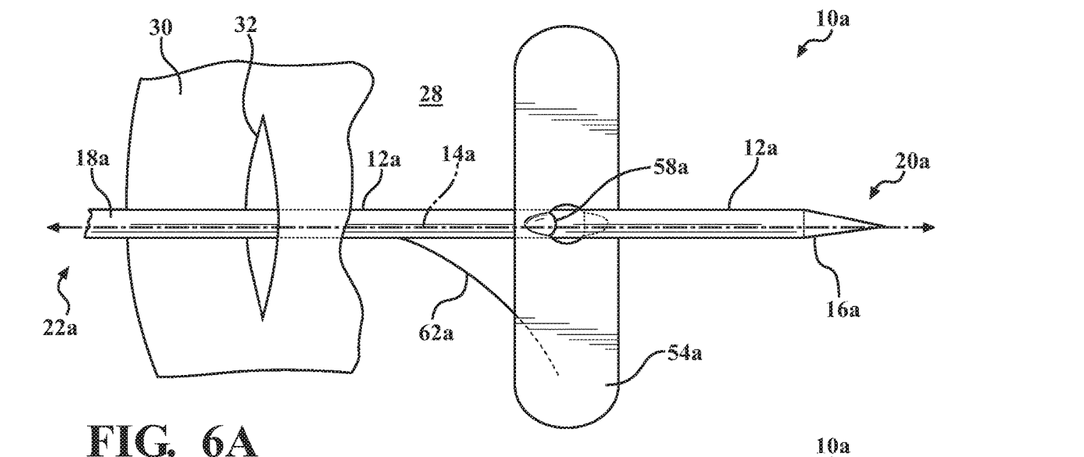
FIG. 6A is a top view of the second exemplary embodiment of the present disclosure positioned within the anterior chamber of an eye.
Figure 6B:
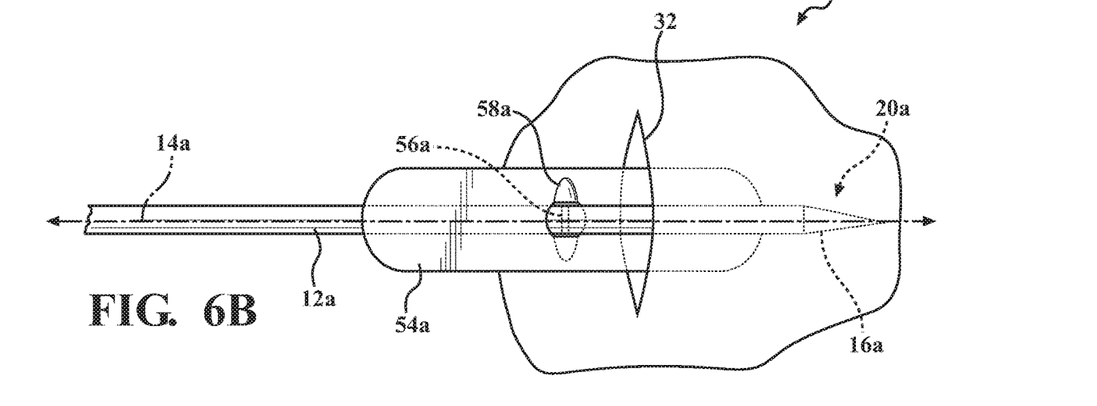
FIG. 6B is a top view of the second exemplary embodiment of the present disclosure during insertion into the anterior chamber of an eye.

The exemplary light redirecting structure 24a includes a panel 54a. The exemplary panel 54a is pivotally mounted on the exemplary body 12a. The exemplary light redirecting structure 24a includes a pivot pin 56a passing through the exemplary body 12a. A first hub 58a is formed on one side of the exemplary panel 54a and a second hub 60a is formed on a second side of the exemplary panel 54a. At a first end, the exemplary pivot pin 56a can be received in the first hub 58a. At a second end, the exemplary pivot pin 56a can be received in the second hub 60a. The exemplary pivot pin 56a can be connected to the hubs 58a, 60a with ball and socket joints. The exemplary light redirecting structure 24a is thus pivotable relative to the exemplary body 12a about a plurality of pivot axes. FIG. 6a shows the exemplary light redirecting structure 24a at a first end limit of travel and FIG. 6B shows the exemplary light redirecting structure 24a at a second end limit of travel.

The exemplary device insertion tool 10a can also include an elongate member 62a to pivot the exemplary panel 54a. The elongate member 62a can be a wire extending between a first end that is interconnected to at least one exemplary panel 54a and a second end that is spaced from the first end. The elongate member 62a can extend through at least part of the exemplary body 12a and be configured to move within the exemplary body 12a to move the at least one exemplary panel 54a. The second end can extend out of the aft end 18a and be grasped by the healthcare provider. Pulling the second end can result in the exemplary panel 54a pivoting to the second end limit of travel (FIG. 6B) and pushing the second end can result in the exemplary panel 54a pivoting to the first end limit of travel (FIG. 6A). The exemplary panel 54a can be pivoted to the second end limit of travel (FIG. 6B) for insertion through the incision 32 and can be pivoted to the first end limit of travel (FIG. 6A) when fully positioned in the chamber 28 to redirect light.

In various embodiments of the present disclosure, a panel can be flexible and elastic so that it can be deformed prior to being inserted into the anterior chamber 28 and then return to its static shape after placement in the chamber 28. Such a panel could further be deformed for removal from the chamber 28. Various embodiments of the present disclosure could include other forms of interconnection between a panel and a body, such as hinges, groove and runner, springs or other mechanism so that the profile of the panel can occupy the same plane as that of the handle portion 22a as it is being introduced through an ocular incision 32 and reform to a different orientation relative to the handle portion 22a if necessary to ideally perform its functions as a goniomirror. After insertion into the anterior chamber 28, the change in configuration could be actuated by a rod/spring being depressed at the end of the handle outside the eye. The change in configuration can be reversible through the same mechanism to allow withdrawal of the instrument after the mirror has been used.

The orientation of the exemplary light redirecting structure 24a in relation to the body 12a can have a variation of at least two configurations. First, a "see-saw" variation can be applied wherein the reflecting surface of the exemplary light redirecting structure 24a is above the handle portion 22a proximal to the pivot axis, lateral to the handle portion 22a at the pivot axis, and below the handle portion 22a distal to the hinge (relative to the incision when exemplary light redirecting structure 24a is in the eye). The angle between the handle portion 22a and the exemplary light redirecting structure 24a can be variably and controllably increased and decreased after placement in the anterior chamber 28 to allow optimal visualization.

A "sail" variation can be applied wherein the reflective surface plane is aligned with the axis 14a during insertion but the handle portion 22a rotated on the axis 14a after the exemplary light redirecting structure 24a is in the anterior chamber 28 so that the exemplary light redirecting structure 24a can assume a width substantially wider than the corneal incision 32 and allow optical benefits of a wider field of view, as well as other optical benefits conferred by wider size that depend on the optical nature and power of the exemplary light redirecting structure 24a. The exemplary light redirecting structure 24a can be fixed to the handle portion 22a with a hinge that allows rotation so that plane of the exemplary light redirecting structure 24a can be approximately 3 mm high and approximately 6-12 mm wide or more. The exemplary light redirecting structure 24a can be arranged as a flexible, slightly curved surface that can switch from a plane parallel to the handle portion 22a when it is inserted through the corneal incision 32, to a plane that is approximately perpendicular to the long axis 14a of the handle portion 22a, and oblique to a visual axis of the surgical microscope used with the exemplary device insertion tool 10a.

It is also noted that the exemplary light redirecting structure 24a could include a non-planar structure pivotally mounted to the body 12a, such as a dome. In such an embodiment, the exemplary light redirecting structure 24a would present a convex toward the front end 16a. The axis of pivoting movement of such an embodiment could pass through the center of curvature of the dome or could be spaced from the center of curvature of the dome.

Figure 7:
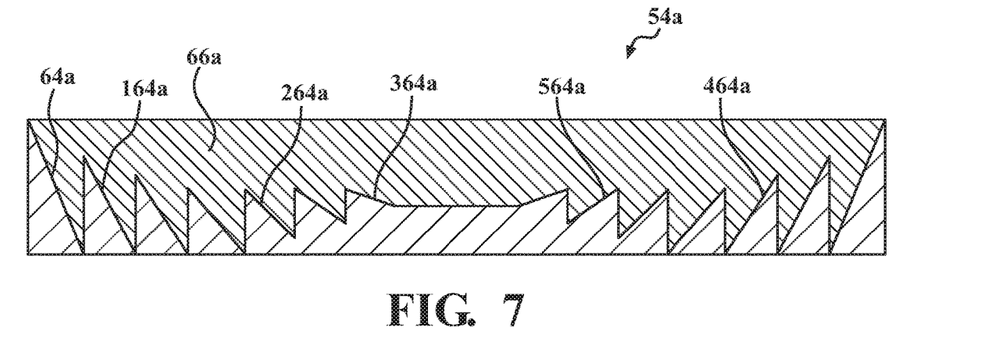
FIG. 7 is a cross-sectional view taken through section lines 7-7 in FIG. 5.

Referring now to FIG. 7, the exemplary light redirecting structure 24a comprises a Fresnel array of mirrors. The panel 54a defines a plurality of planar surfaces directed at the forward end 16a. Fourteen planar surfaces are shown in FIG. 7 and some are referenced at 64a, 164a, 264a, 364a, 464a, 564a. Each of the planar surfaces is a mirror. The planar surfaces 64a, 164a, 264a, 364a, 464a, 564a can redirect light traveling from the forward end 16a toward the aft end 18a transverse to the central longitudinal axis 14a. It is noted that the portion of the exemplary panel 54a referenced at 66a is a cover formed of transparent material that prevents the edges between the panels from being exposed.

Fresnel mirror arrangements with or without nanolens technology can provide optical properties independent of shape and profile of device insertion tool. The required optical properties of a plano, spherocylindrical, or aspheric mirrors can be achieved without the curvature and shape constraints imposed by conventional reflecting surfaces by the use of a Fresnel arrangement of reflecting elements. Furthermore, the use of a Fresnel array of reflecting elements allows a mirror shape and profile to be constructed independent of the curvature constraints of conventional reflecting surfaces so that, for example, a concave mirror optical effect can be rendered by a convex-shaped Fresnel mirror array, and vice versa. Similarly, a flat Fresnel mirror array can render a spherocylindrical optical effect that can be concave, convex or aspheric as necessitated by the requirements of visualization. While the Fresnel array may degrade the optical quality of the image, the degradation may be minimized by (a) designing the spacing and interface qualities of the array to minimize optical aberrations; (b) incorporation aspheric and/or non-planar patterns to minimize optical aberrations; (c) adjusting the relative depth of the Fresnel arrays to minimize optical aberrations; or (d) incorporating nanophotonic lens technology to minimize optical aberrations and increase optical resolution. Other benefits of Fresnel array mirrors and nanolens technology include potential increase in depth of field, reduced mirror thickness, reduced mirror size and enhanced optical resolution.

Figure 8:
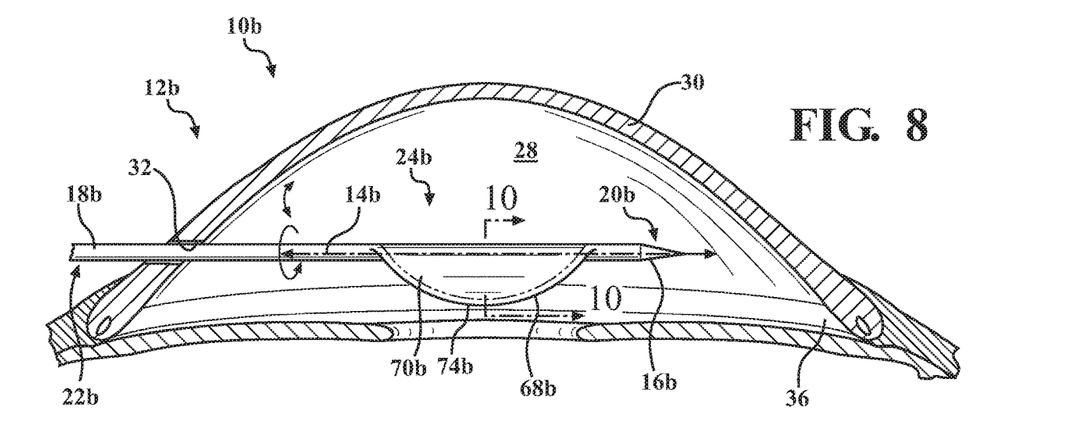
FIG. 8 is a side view of a third exemplary embodiment of the present disclosure positioned within the anterior chamber of an eye.

In a third embodiment of the present disclosure, shown in FIGS. 8-11, a device insertion tool 10b includes a body 12b. The exemplary body 12b extends along a central longitudinal axis 14b between a forward end 16b and an aft end 18b. The exemplary body 12b terminates at the forward end 16b and at the aft end 18b. The exemplary body 12b includes a device mount portion 20b at the forward end 16b. The exemplary device mount portion 20b is configured to hold a device during insertion of the device in an eye. The exemplary body 12b also includes a handle portion 22b at the aft end 18b. The exemplary handle portion 22b is configured to be held by a healthcare provider during insertion of the device in the eye. A healthcare provider can be an ophthalmologist and/or an eye surgeon. The exemplary body 12b is configured to be inserted into an anterior chamber of the eye, through an incision in a cornea of the eye, with the device mounted on the device mount portion 20b at the forward end 16b. In FIG. 8, the anterior chamber is referenced at 28, the cornea is referenced at 30, the incision at 32, and the trabecular meshwork is referenced at 36. A device such as an stent can be inserted into the trabecular meshwork 36 using the device insertion tool 10b.

The device insertion tool 10b also includes a light redirecting structure 24b engaged with the exemplary body 12b between the forward end 16b and the aft end 18b. The exemplary light redirecting structure 24b is also configured to be inserted into the anterior chamber 28 of the eye, through the incision 32 in the cornea 30 of the eye during positioning of the device in the eye. The light redirecting structure 24b can be at least one mirror. The light redirecting structure 24b can be directed at the forward end 16b and can be configured to redirect light traveling from the forward end 16b toward the aft end 18b transverse to the central longitudinal axis 14b. The light traveling from the forward end 16b is light that is reflected off of the structures of the eye. The redirected light can be seen by the healthcare provider and thus allows the healthcare provider to see the location of insertion of the device in the eye.

The exemplary light redirecting structure 24b includes a bladder portion 68b and a reflective surface coating 70b. The exemplary bladder portion 68b is mounted on the exemplary body 12b. The exemplary reflective surface coating 70b disposed on at least part of an outer surface of the exemplary bladder portion 68b. The reflective surface coating 70b can be adhered to the bladder portion with adhesive.

Figure 9:
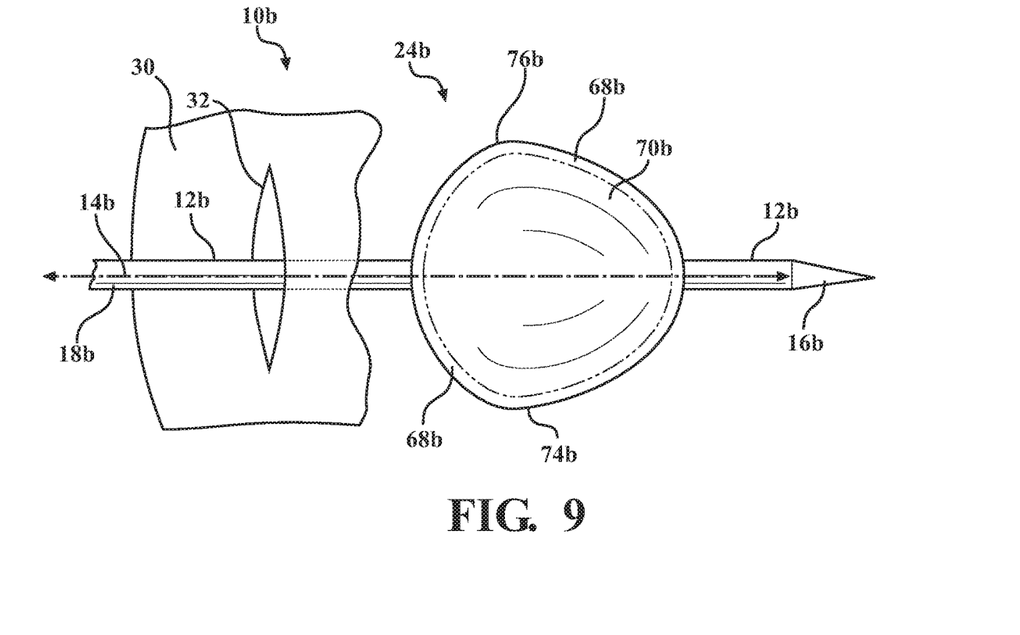
FIG. 9 is a top view of the third exemplary embodiment of the present disclosure positioned within the anterior chamber of an eye.
Figure 10:
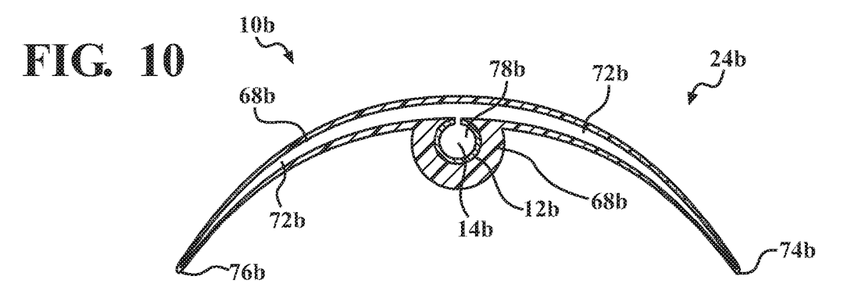
FIG. 10 is a cross-sectional view taken through section lines 10-10 in FIG. 8.
Figure 11:
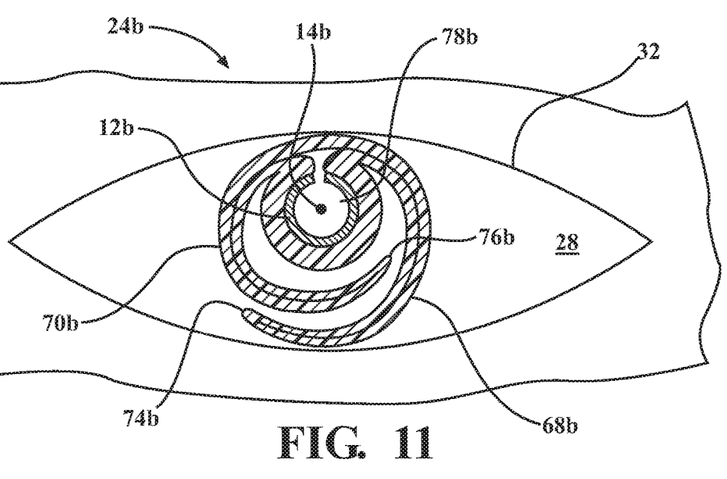
FIG. 11 is a cross-sectional view taken in the plane of cross-section of FIG. 10, but taken as the third exemplary embodiment of the present disclosure is being inserted into the anterior chamber of an eye.

The exemplary bladder portion 68b is selectively, elastically expandable. The exemplary bladder portion 68b is configured to expand in operation from a retracted configuration to an expanded configuration and elastically return to the retracted configuration from the expanded configuration when not in operation. FIGS. 8-10 show the exemplary bladder portion 68b in the expanded configuration. FIG. 11 shows the exemplary bladder portion 68b in the retracted configuration. The exemplary bladder portion 68b assumes, generally, a shape that is relatively short and cylindrical and further is bent about the axis 14b when in the expanded configuration. The exemplary bladder portion 68b assumes, generally, a bent pancake shape when in the expanded configuration. When in the retracted configuration, the portions of the periphery of the exemplary bladder portion 68b, referenced at 74b and 76b, more tightly wrap around the body 12b, as best shown in FIG. 11. The exemplary bladder portion 68b wraps around the exemplary body 12b when in the retracted configuration.

An interior 72b of the exemplary bladder portion 68b is in fluid communication with an interior 78b of the exemplary body 12b. Pressurized fluid can enter the interior 72b of the exemplary bladder portion 68b from the interior 78b of the exemplary body 12b. The exemplary bladder portion 68b unfurls in response to pressurized fluid entering the interior 72b of the exemplary bladder portion 68b from the interior 78b of the exemplary body 12b. The exemplary bladder portion 68b furls (or returns the retracted configuration) in response to pressurized fluid leaving the interior 72b of the exemplary bladder portion 68b. The exemplary bladder portion 68b can thus be selectively inflated as needed. It is noted that, in other embodiments of the present disclosure, a bladder portion could be shaped differently. For example, in one or more embodiments of the present disclosure, a bladder portion could take a bulbous shape when inflated and not a pancake-like shape.

In operation, a healthcare provider can grasp the handle portion 22b of the body 12b to adjust the position of the reflective surface coating 70b to optimize the view of the area of insertion. The tool 10b can be rotated about the axis 14b and/or can be tilted whereby the forward end 16b is lowered relative to the aft end 18b.

In a fourth embodiment of the present disclosure, shown in FIGS. 12-15, a device insertion tool 10c includes a body 12c. The exemplary body 12c extends along a central longitudinal axis 14c between a forward end 16c and an aft end 18c. The exemplary body 12c terminates at the forward end 16c and at the aft end 18c. The exemplary body 12c includes a device mount portion 20c at the forward end 16c. The exemplary device mount portion 20c is configured to hold a device during insertion of the device in an eye. One exemplary device that can be inserted in an eye with the device insertion tool 10c is a stent, such as the iStent® product. The exemplary device mount portion 20c can shaped to include piercing tip to form an opening for the device in the tissue of the eye and also a tubular portion to hold the device prior to insertion and guide movement of the eye during insertion.

Figure 12:
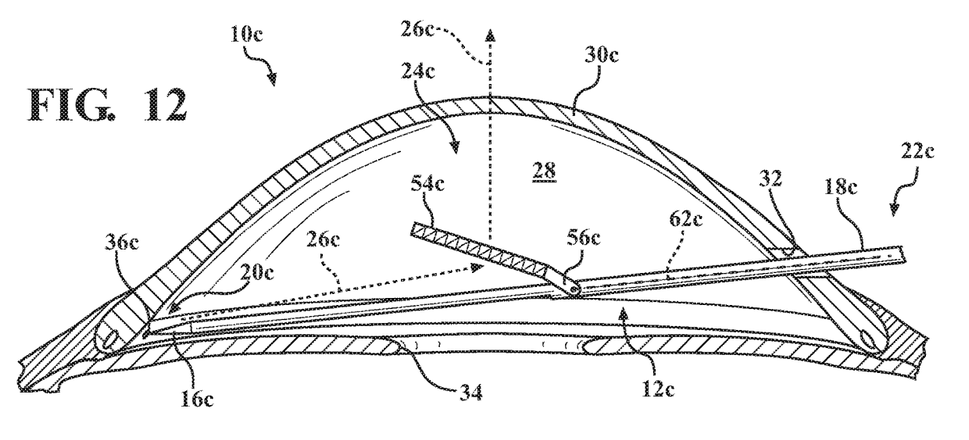
FIG. 12 is a side view of a fourth exemplary embodiment of the present disclosure positioned within the anterior chamber of an eye.

The exemplary body 12c also includes a handle portion 22c at the aft end 18c. The exemplary handle portion 22c is configured to be held by a healthcare provider during insertion of the device in the eye. A healthcare provider can be an ophthalmologist and/or an eye surgeon. The exemplary body 12c is configured to be inserted into an anterior chamber of the eye, through an incision in a cornea of the eye, with the device mounted on the device mount portion 20c at the forward end 16c. In FIG. 12, the anterior chamber is referenced at 28, the cornea is referenced at 30, the incision at 32, the pupil is referenced at 34, and the trabecular meshwork is referenced at 36. A device such as an stent can be inserted into the trabecular meshwork 36 using the device insertion tool 10c.

Figure 13:
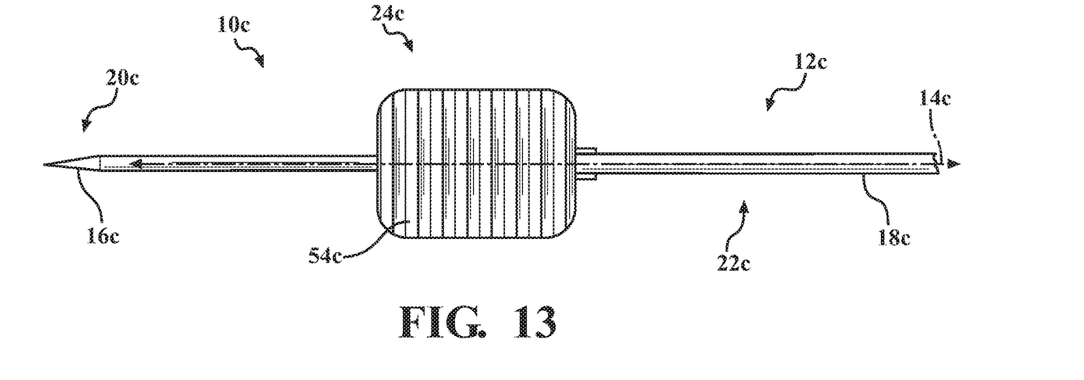
FIG. 13 is a top view of the fourth exemplary embodiment of the present disclosure when positioned within the anterior chamber of an eye.
Figure 14:
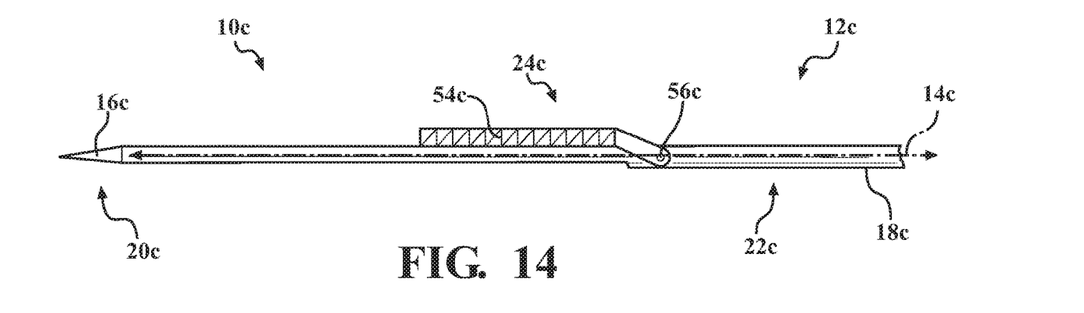
FIG. 14 is a side view of the fourth exemplary embodiment of the present disclosure when being inserted into the anterior chamber of an eye.

The device insertion tool 10c also includes a light redirecting structure 24c engaged with the exemplary body 12c between the forward end 16c and the aft end 18c. Engagement between the light redirecting structure 24c and the exemplary body 12c can also be defined by the light redirecting structure 24c mounted on the exemplary body 12c.

The exemplary light redirecting structure 24c is also configured to be inserted into the anterior chamber of the eye, through the incision in the cornea of the eye during positioning of the device in the eye. The light redirecting structure 24c can be directed at the forward end 16c and can be configured to redirect light traveling from the forward end 16c toward the aft end 18c transverse to the central longitudinal axis 14c. The light traveling from the forward end is light that is reflected off of the structures of the eye. The redirected light can be seen by the healthcare provider and thus allows the healthcare provider to see the location of insertion of the device in the eye. In FIG. 12, the arrows referenced at 26c represents the movement of light from the forward end 16c, which is also the location of insertion of the device in the eye and redirection of the light transverse to the central longitudinal axis 14c for viewing by the healthcare provider.

The exemplary light redirecting structure 24c includes a panel 54c. The exemplary panel 54c is pivotally mounted on the exemplary body 12c. The exemplary light redirecting structure 24c includes a pivot pin 56c passing through the exemplary body 12c. The exemplary light redirecting structure 24c is thus pivotable relative to the exemplary body 12c about a single axis. FIG. 12 shows the exemplary light redirecting structure 24c at a first end limit of travel and FIG. 14 shows the exemplary light redirecting structure 24c at a second end limit of travel. The first end limit of travel correspond to an "in use" or "in operation" position and the second end limit of travel corresponds to a retracted position. The planar panel 54c extends flush with the exemplary body 12c when in the second/retracted position and extends transverse to the exemplary body 12c when in the first position.

The exemplary device insertion tool 10c can also include an elongate member 62c to pivot the exemplary panel 54c. The elongate member 62c can be a wire extending between a first end that is interconnected to at least one exemplary panel 54c and a second end that is spaced from the first end. The elongate member 62c can extend through at least part of the exemplary body 12c and be configured to move within the exemplary body 12c to move the at least one exemplary panel 54c. The second end can extend out of the aft end 18c and be grasped by the healthcare provider. Pulling the second end can result in the exemplary panel 54c pivoting to the second end limit of travel (FIG. 14) and pushing the second end can result in the exemplary panel 54c pivoting to the first end limit of travel (FIG. 12). The exemplary panel 54c can be pivoted to the second end limit of travel (FIG. 14) for insertion through the incision 32 and can be pivoted to the first end limit of travel (FIG. 12) when fully positioned in the chamber 28 to redirect light.

Figure 15:
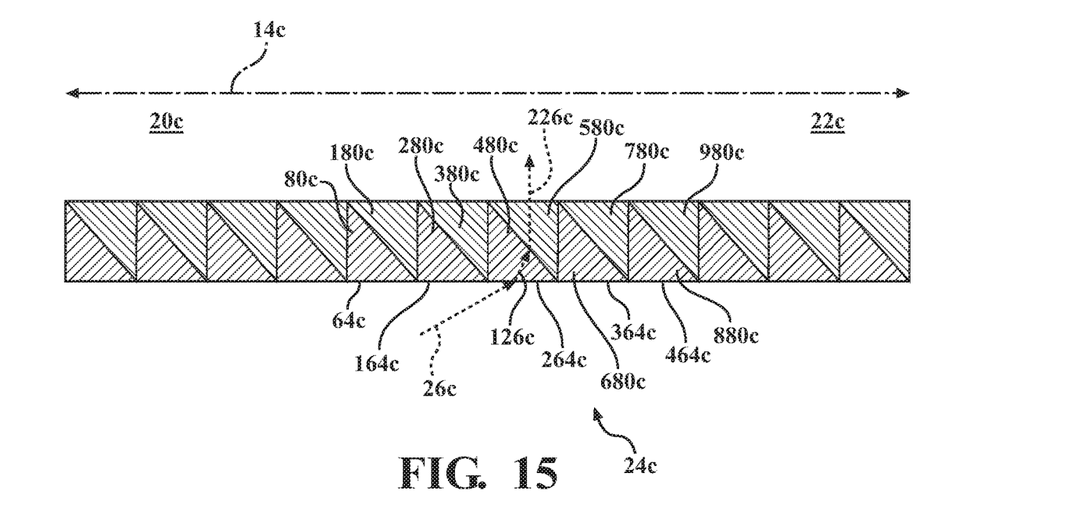
FIG. 15 is a side view of a panel of the fourth exemplary embodiment of the present disclosure.

Referring now to FIG. 7, the exemplary light redirecting structure 24c comprises a Fresnel array of prisms. FIG. 15 is a view of the panel 54c in which a portion is referenced by numbers, including prisms 80c, 180c, 280c, 380c, 480c, 580c, 680c, 780c, 880c, 980c. The exemplary plurality of prisms 80c, 180c, 280c, 380c, 480c, 580c, 680c, 780c, 880c, 980c are arranged side-by-side and form the planar panel 54c.

The prisms 80c, 280c, 480c, 680c, 880c define a plurality of planar surfaces directed at the forward end 16a. Five planar surfaces are shown in FIG. 15 and are referenced at 64c, 164c, 264c, 364c, 464c. Each of the planar surfaces is transparent redirects light traveling from the forward end 16a toward the aft end 18a transverse to the central longitudinal axis 14c. This shown by the transition from arrow 26c and arrow 126c. Upon passing the junction of prisms 480c and 580c, the light is again redirected. This shown by the transition from arrow 126c and arrow 226c. The refractive index of the exemplary prisms 80c, 280c, 480c, 680c, 880c is greater than the refractive index of the aqueous humor in the chamber 28. The refractive index of the exemplary prisms 180c, 380c, 580c, 780c, 980c is less than the refractive index of the aqueous humor in the chamber 28.

In another embodiment of the present disclosure, a camera can be positioned on the body of the tool rather than a light redirecting structure. The cameras can be multiple and located at different viewing angles to provide a stereoscopic view of the anterior chamber structures by virtue of parallax. The camera can include a wireless transmitter to transmit images captured by the camera to obviate the need for wiring from the camera. Images captured by the camera can be displayed on a monitor viewable by the healthcare provider as the tool is being utilized.

Figure 16:
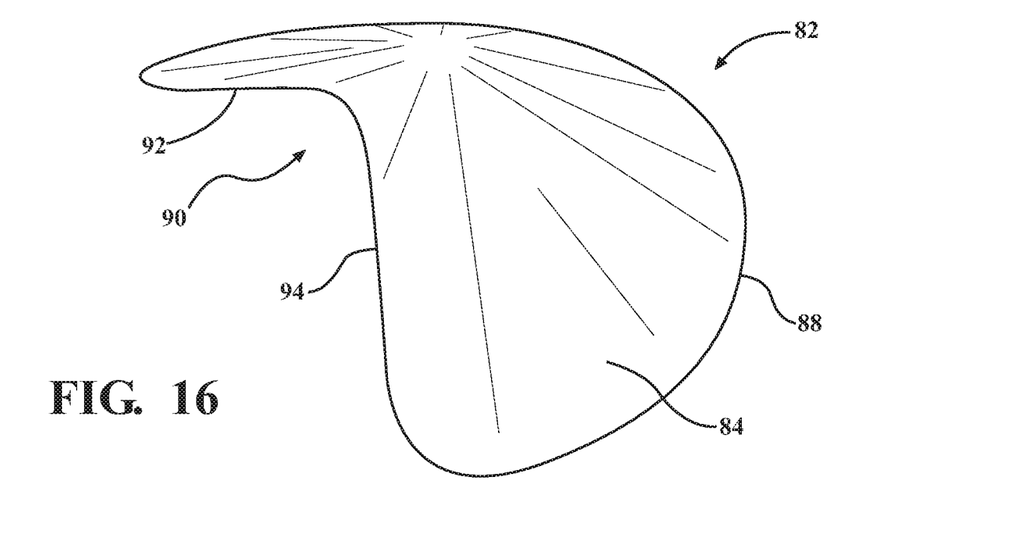
FIG. 16 is a perspective view, generally from above, of a mirror according to another aspect of the present disclosure.
Figure 17:
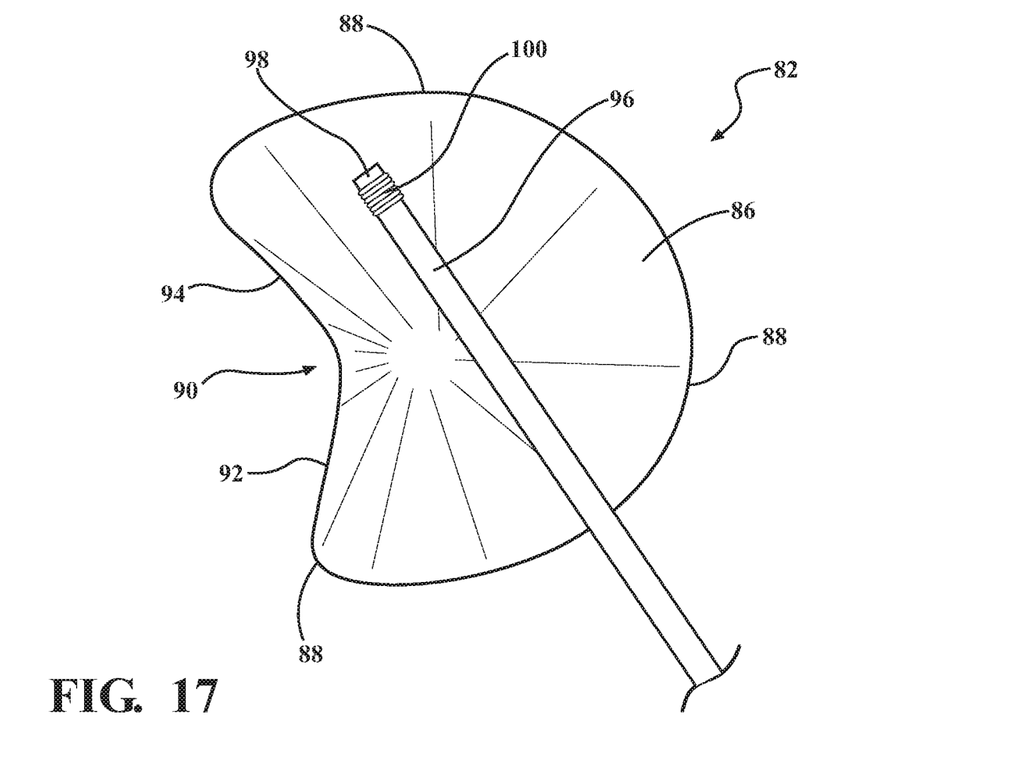
FIG. 17 is a bottom view (looking up) of the mirror shown in FIG. 16.
Figure 18:
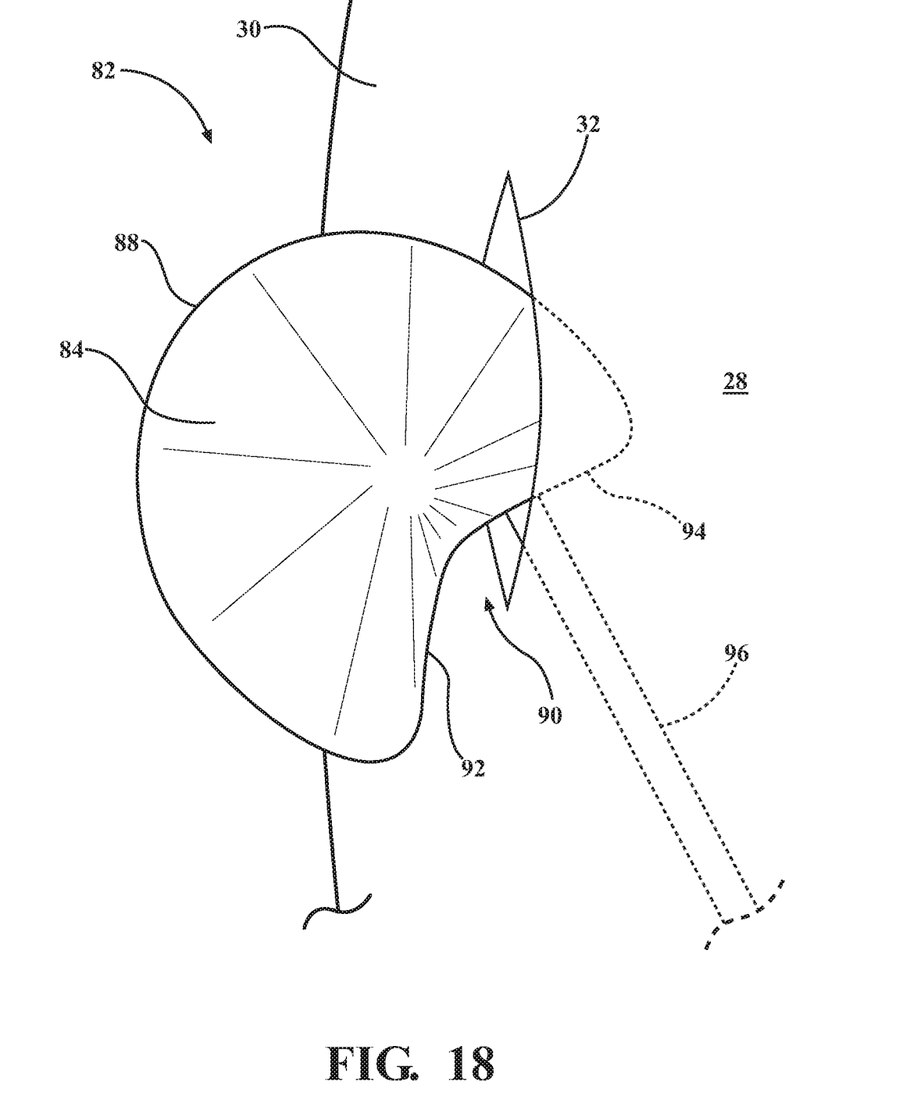
FIG. 18 is a view of insertion of the mirror shown in FIGS. 16 and 17 into the eye.

Referring now to FIGS. 16-18, the present disclosure also includes a mirror that is separate from a surgical instrument. Generally, in addition to the main corneal incision performed during cataract surgery, one or more smaller incisions known as paracenteses can be required during surgery of the anterior segment of the eye. One of these paracenteses can be used to introduce a glaucoma surgical device, such as the embodiments described above, and a gonioscopic mirror can be introduced through the main incision. The advantages of this approach include the ability to manipulate the mirror independent of the glaucoma surgery device for optimal visualization.

A "pop-up" mirror 82 includes an upper surface 84, a lower surface 86, and a perimeter 88. The upper surface 84 defines a mirror operable to reflect light. The perimeter 88 defines a notch 90. The notch 90 is defined between two confronting edges 92, 94. The exemplary edges 92, 94 are part of the perimeter 88.

As shown particularly in FIG. 17, a handle 96 can be flexibly attached to the lower surface 86 of the mirror 82. A mounting hub 98 can project from the lower surface 86 and can interconnect with the handle 96. A spring 100 can be interposed between the hub 98 and the handle 96 to enhance the flexibility between the two structures. Other interconnection structures can be applied in other embodiments, such as grooves and rollers.

The exemplary mirror 82 thus has a roughly three-quarter circle profile allowing it to be placed through and incision smaller than its effective diameter when it acts as a mirror. As shown in FIG. 18, the flexible joint defined between the handle 96 and the mirror 82 allows the mirror 82 to be dragged/pushed through an incision 32. During insertion the mirror 82 may be elastically deformed. Upon placement in the chamber 82, the mirror 82 can return to its static shape for viewing. Similarly, the mirror 82 can be pulled/dragged out of the chamber 28 through the incision 32. It is noted that handle 96 can be introduced to the chamber 28 through an incision other than the incision 32. While in the chamber 28, the mirror 82 can be placed on the iris during the surgical procedure.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or subcombinations that are disclosed herein is hereby unconditionally reserved. The use of the word "can" in this document is not an assertion that the subject preceding the word is unimportant or unnecessary or "not critical" relative to anything else in this document. The word "can" is used herein in a positive and affirming sense and no other motive should be presumed. More than one "invention" may be disclosed in the present disclosure; an "invention" is defined by the content of a patent claim and not by the content of a detailed description of an embodiment of an invention.

What is claimed is:

1. A device insertion tool comprising:
   a body extending along a central longitudinal axis between a forward end and an aft end, said body including a device mount portion at said forward end configured to hold an optic during insertion of the optic in an eye, said body also including a handle portion at said aft end configured to be held by a healthcare provider during insertion of the optic in the eye, wherein said body is configured to be inserted into an anterior chamber of the eye, through an incision in a cornea of the eye, with the optic mounted on said device mount portion at said forward end during positioning of the optic in the eye; and
   a light redirecting structure engaged with said body between said forward end and said aft end, said light redirecting structure being one of at least one mirror and at least one prism, said light redirecting structure directed at said forward end and configured to redirect light traveling from said forward end toward said aft end transverse to said central longitudinal axis.

2. The device insertion tool of claim 1 wherein said body and said light redirecting structure are integrally formed and unitary.

3. The device insertion tool of claim 1 wherein said light redirecting structure further comprises:
a first surface portion that faces and is concave toward said forward end; and
a second surface portion that faces and is convex toward said forward end, said first surface portion and said second surface portion adjacent to one another and blending together.

4. The device insertion tool of claim 1 wherein a width of said light redirecting structure and a width of said forward end is defined along an axis perpendicular to said central longitudinal axis and wherein a maximum width of said light redirecting structure is greater than a maximum width of said forward end.

5. The device insertion tool of claim 1 wherein a width of said light redirecting structure is defined along an axis perpendicular to said central longitudinal axis and wherein said width of said light redirecting structure varies along said central longitudinal axis, said width of said light redirecting structure having a first value at a first portion of said light redirecting structure that is closest to said forward end, said width of said light redirecting structure having a second value at a second portion of said light redirecting structure that is closest to said aft end, said width of said light redirecting structure having a third value at a third portion of said light redirecting structure that disposed between the first position and the second position along said central longitudinal axis, said third value greater than said first value and greater than said second value, and said body and said light redirecting structure have substantially the same width at said first portion and said second portion.

6. The device insertion tool of claim 1 wherein said light redirecting structure defines a planar surface directed at said forward end and configured to redirect light traveling from said forward end toward said aft end transverse to said central longitudinal axis.

7. The device insertion tool of claim 1 wherein said light redirecting structure is further defined as pivotally mounted on said body.

8. The device insertion tool of claim 7 wherein said light redirecting structure is pivotable relative to said body about a single pivot axis.

9. The device insertion tool of claim 7 wherein said light redirecting structure is pivotable relative to said body about a plurality of pivot axes.

10. The device insertion tool of claim 1 wherein said light redirecting structure further comprises a Fresnel array.

11. The device insertion tool of claim 10 wherein said Fresnel array is further defined as an array of mirrors.

12. The device insertion tool of claim 10 wherein said Fresnel array is further defined as an array of prisms.

13. The device insertion tool of claim 1 wherein said light redirecting structure is further defined as selectively, elastically expandable, said light directing structure configured to expand in operation from a retracted configuration to an expanded configuration and elastically return to said retracted configuration from said expanded configuration when not in operation.

14. The device insertion tool of claim 13 wherein said light redirecting structure is further defined as wrapped around said body when in said retracted configuration.

15. The device insertion tool of claim 1 said light redirecting structure is further defined as at least one prism.

16. The device insertion tool of claim 1 wherein said body and said light redirecting structure are unitary and said light redirecting structure includes at least one of a first surface portion that is concave and a second surface portion that is convex and wherein light from an insertion location within the eye is redirected off of said at least one of said first surface portion and said second surface portion.

17. The device insertion tool of claim 1 wherein said light redirecting structure is further defined as including at least one panel pivotally mounted on said body.

18. The device insertion tool of claim 17 further comprising:
an elongate member extending between a first end that is interconnected to at least one panel and a second end that is spaced from said first end, said elongate member extending through at least part of said body and configured to move within said body to move said at least one panel.

19. The device insertion tool of claim 1 wherein said light redirecting structure further comprises:
a bladder portion mounted on said body, an interior of said bladder portion in fluid communication with an interior of said body whereby pressurized fluid can enter said interior of said bladder portion from said interior of said body, wherein said bladder portion unfurls in response to pressurized fluid entering said interior of said bladder portion from said interior of said body, and wherein said bladder portion furls in response to pressurized fluid leaving said interior of said bladder portion; and
a reflective surface coating disposed on at least part of an outer surface of said bladder portion.

20. The device insertion tool of claim 1 said light redirecting structure further comprising:
a plurality of prisms arranged side-by-side and forming a planar panel, said planar panel connected to said body with a pivot pin wherein said planar panel is pivotable between a first position and a second position, wherein said planar panel extends flush with said body when in said first position and extends transverse to said body when in said second position.

* * * * *